United States Patent [19]

Maggio

[11] Patent Number: 4,789,631
[45] Date of Patent: Dec. 6, 1988

[54] IMMUNOASSAY FOR ANTI-DIROFILARIA IMMITIS ANTIBODY

[75] Inventor: Edward T. Maggio, San Diego, Calif.

[73] Assignee: Synbiotics Corporation, San Diego, Calif.

[21] Appl. No.: 581,347

[22] Filed: Feb. 17, 1984

[51] Int. Cl.$^4$ .................. G01N 33/53; G01N 33/545; G01N 33/569

[52] U.S. Cl. ...................................... 435/7; 424/85.8; 435/810; 436/518; 436/531; 436/534; 436/548; 530/387; 530/413

[58] Field of Search ................... 435/7, 240, 948, 810; 436/531, 534, 548, 809, 518; 424/85; 935/90, 92, 108, 110; 260/112 R; 530/387, 413

[56] References Cited

U.S. PATENT DOCUMENTS

| | | | |
|---|---|---|---|
| 4,205,954 | 6/1980 | Babson | 436/534 X |
| 4,322,495 | 3/1982 | Kato | 435/7 |
| 4,362,531 | 12/1982 | de Steenwinkel et al. | 436/534 X |
| 4,499,014 | 2/1985 | Estis | 260/112 R |
| 4,524,025 | 6/1985 | Geltosky | 260/112 R |

FOREIGN PATENT DOCUMENTS

| | | | |
|---|---|---|---|
| WO81/02899 | 10/1981 | World Int. Prop. O. | 935/108 |
| WO83/03678 | 10/1983 | World Int. Prop. O. | 436/548 |

OTHER PUBLICATIONS

Chemical Abstracts, I, 101: 126318g (1984).
Chemical Abstracts, II, 101: 228444n (1984).
Plotz et al., "American J. of Med." (1956), pp. 893–896.
Nakane et al., "J. of Histochemistry and Cytochemistry", vol. 22, No. 12 (1974), pp. 1084–1091.
Axén et al., "Nature," vol. 214 (1967), pp. 1302–1304.
Wong et al., "Transactions of the Royal Soc. of Tropical Medicine and Hygiene," vol. 63, No. 6 (1969), pp. 796–800.
Singer et al., "American J. of Med." (1956), pp. 888–892.
Köhler et al., *Nature*, vol. 256 (1975), pp. 495–497.
Galfre et al., *Nature*, vol. 266 (1977), pp. 550–552.
Grieve et al., *Am. J. Vet. Res.*, vol. 42(1) (1981), pp. 66–69.
Kearney et al., *J. of Immunol.*, vol. 123(4) (1979), pp. 1548–1550.

*Primary Examiner*—Sidney Marantz
*Attorney, Agent, or Firm*—Donald G. Lewis

[57] ABSTRACT

A serum antibody assay for assaying a serum sample is described which has diagnostic value for determining the presence of a specific serum antibody which may be indicative of an infection by a specific microorganism. The serum antibody assay has an enhanced diagnostic value because it can eliminate interference by selected cross-reactive antibodies which are directed against one or more other microorganisms to which the assay is not directed and which may be present in the serum sample with a clinically significant frequency. The serum antibody assay uses an immunologically purified fraction of antigenic material derived from the specific microorganism to which assay is directed. The immunologically purified fraction of antigenic material includes immunologically distinguishable components of the antigenic material. These immunologically distinguishable components are reactive with the antibodies to be assayed and are nonreactive with certain antibodies not to be assayed, even where these certain antibodies not to be assayed are cross-reactive with antigen from the microorganism to be diagnosed. The immunologically distinguishable components are made using an immunoadsorption method. The immunoadsorption method may be specially screened monoclonal antibodies which bind only the immunologically distinguishable components. Alternatively, the immunoadsorption method may use polyclonal antibodies which bind immunologically cross-reactive components and leave the immunologically distinguishable components unbound.

8 Claims, No Drawings

IMMUNOASSAY FOR ANTI-DIROFILARIA IMMITIS ANTIBODY

BACKGROUND OF THE INVENTION

This invention relates to a serum antibody assay used as a diagnostic tool to determine if a particular microorganism might be responsible for a disease state. More particularly, this invention relates to the materials and methods of an assay for serum antibody directed against the particular microorganism which is constructed so as to eliminate false positives caused by the cross-reactivity of other antibodies directed against other microorganisms not targeted by the assay and not the subject of diagnosis.

Frequently, specific serum antibodies can serve as an indirect indicator of a specific disease. A patient's immunogenic response to an infection by a microorganism produces specific antibodies which recognize antigenic sites on that microorganism and which have a binding affinity for such antigenic sites. The detection or measurement of these specific antibodies in the patient's serum provides an indirect method to identify the specific microorganism responsible for the disease. The detection or measurement of these specific antibodies serves as a diagnostic tool for the clinician and enables the clinician to direct therapeutic action against the specific microorganism.

Typically, an antibody assay includes a step in which a sample of the patient's serum is combined with antigenic material derived from the suspect microorganism, i.e. the microorganism to which the assay is targeted. The assay result is positive if serum antibody is found to bind to the antigenic material. However, unless precautionary steps are taken, the positive result of an assay can be, in fact, a false positive.

The patient's serum may contain cross-reactive antibody. Cross-reactive antibody is a product of an immunogenic response to a nontarget microorganism, i.e., a microorganism which is different than the microorganism to which the assay is targeted. However, cross-reactive antibody may bind to the antigenic material used in the assay. Both the target and nontarget microorganisms may share certain structural features among their respective antigens. Antibody which is specific for such a nontarget microorganism may also cross-react with antigen derived from the target microorganism. The presence of cross-reactive antibody can cause false positives in an assay which utilizes antigen derived from the target microorganism. Such cross-reactivity results in a reduction of the diagnostic utility of the assay.

The prior art teaches that this problem of cross-reactivity can be overcome by pretreatment of the patient's serum with antigen derived from the nontarget microorganism having structurally similar antigenic sites to the target microorganism. Such pretreatment will neutralize the cross-reactive antibody, if present, by causing the cross-reactive antibody to bind to the antigen derived from the nontarget microorganism. Such pretreatment will thereby prevent the cross-reactive antibody from binding the antigen of the target microorganism utilized by the assay. An example of an antibody assay with pretreatment is given by Grieve (Grieve, R., et al, American Journal of Veterinary Research, vol. 42 (1), pages 66–69 (1981)). Grieve describes an assay for antibody against Dirofilaria immitis in canine serum which requires a pretreatment of canine sera with Toxocara canis antigen to neutralize anit-T. canis antibodies. Thereafter, the pretreated sera may be tested for anti-D. immitis antibodies substantially without further interference. Unfortunately, such antigen pretreatments introduce additional steps into the assay procedure, which steps may be time consuming and laborious and which may provide additional opportunity for the introduction of error into the assay protocol. Also, additional pretreatments must be made for each nontarget microorganism which is known to elicit cross-reactive antibody to the antigen of the target microorganism.

The present invention addresses the inability of existing antibody assays to measure, without pretreatment, the presence of a specific antibody type as an indication of a specific target microorganism responsible for a disease state, without the risk of the assay yielding a false positive identification caused by cross-reactive serum antibody directed against one or more nontarget microorganisms. For example, the present invention addresses the inability of existing serum antibody assays to detect anti-D. immitis antibody in canine serum so as to diagnose a heartworm infection, without pretreatment of the canine serum and without the risk of obtaining a false positive caused by the cross-reactivity of anti-Toxocara canis antibodies in the canine serum directed against an infection by the intestinal roundworm Toxocara canis.

SUMMARY OF THE INVENTION

The present invention discloses an assay for determining the presence of an antibody type in serum containing cross-reactive antibodies. The assay is used as a diagnostic tool to identify the microorganism against which the antibody type was generated. The assay of this invention does not require pretreatment of the serum to eliminate binding by the cross-reactive antibodies. The assay of this invention requires the use of an immunologically purified fraction of antigenic material derived from the microorganism to which the assay is targeted. The invention also provides immunological methods for obtaining this immunologically purified fraction of the antigenic material. These immunological methods selectively purify the antigenic material derived from the target microorganism and render an immunologically purified fraction of the antigenic material which is essentially nonreactive with one or more antibody types, each antibody type having a specificity for a respective nontarget microorganism, and each having a cross-reactivity for some antigenic component of the target microorganism. The assay of this invention is rendered free of cross-reactivity from these selected antibody types by its use of the immunologically purified fraction of antigenic material obtained by the immunological methods of purification disclosed therein.

The antibody assay of the invention advances the prior art by the use of an immunologically purified fraction of antigenic material. Prior art serum antibody assays used only antigenic material derived by physical methods. The antigenic material, immunologically or physically purified, is attached to a solid phase carrier to form an antigenic reagent. Examples of the solid phase carrier include microtiter wells and latex particles. The serum sample to be assayed is then brought into contact with the antigenic reagent and incubated. If the serum sample contains antibody having a specificity for the antigenic material, binding will occur between the antibody and the antigenic reagent. After the incubation is complete, bound antibody is determined. If the antigenic reagent includes a microtiter well, the serum is first decanted and the well is washed. Then a variety of techniques may be used to detect antibody bound to the well. If the antigenic reagent includes a latex particle, antibody binding is detected by the observation of agglutination of the latex particles.

The use of immunologically purified antigenic material in the antigenic reagent renders the antibody assay of the invention more reliable than prior art antibody assays without pretreatment. Potentially, the use of immunologically purified antigenic material can eliminate cross-reactivity due to an antibody type which is directed against any nontarget microorganism, including nontarget microorganisms having antigenic similarity with the target microorganism but lacking one or more immunologically distinguishable antigenic sites which are present on the target microorganism. If one or more immunologically distinguishable antigenic sites on the target microorganism can be isolated using the immunological purification method of this invention, then cross-reactivity with the corresponding nontarget microorganism can be eliminated. In practice, the scope of the cross-reactivity which can be eliminated for antigenically similar microorganisms may be limited by the physical fractionation and purification steps which preceed the immunological purification step (discussed infra). If all immunologically distinguishable antigenic sites are lost during the physical fractionation and purification steps, then cross reactivity can not be eliminated by this invention. In practice, the scope of the cross-reactivity which can be eliminated may also be limited by the avidity of the immunologically distinguishable antigenic sites. If the avidity of all immunologically distinguishable antigenic sites is excessively low, then cross reactivity may be difficult to eliminate by this invention.

The invention includes two different methods for immunologically purifying antigenic material:
 a. The monoclonal antibody method;
 b. The polyclonal antibody method.

The monoclonal antibody method utilizes monoclonal antibodies having a specificity for one or more components of the antigenic material from the target microorganism, which components are immunologically distinguishable from the antigenic material of the nontarget microorganism. The monoclonal antibodies are obtained from hybridomas derived from lymphocytes directed against the target microorganism. The hybridomas are selected by a double screening process. In the first step, the hybridomas are screened for the production of monoclonal antibody having a binding affinity for a component of the antigenic material derived from the target microorganism. In the second step, the hybridomas selected from the first step are further screened to fine monoclonal antibody which lacks a binding affinity for antigen from the selected nontarget microorganism. The monoclonal antibody selected in the second step is specific for immunologically distinguishable antigenic material derived from the target microorganism.

The monoclonal antibody is then immobilized by attachment to matrix material. A soluble fraction of antigenic material from the target microorganism is then passed over the matrix material. Those components of the antigenic material which are immunologically distinguishable are bound to the monoclonal antibody attached to the matrix material. The unbound components are washed off. The bound components are then released from the matrix material by a releasing agent and collected. The collected components may serve as the immunologically purified fraction of the antigenic material for use in the antibody assay.

The polyclonal antibody method utilizes polyclonal antibody raised against antigenic material derived from one or more selected nontarget microorganisms. This polyclonal antibody is then immobilized by attachment to matrix material. A soluble fraction of the antigenic material from the target microorganism is then passed over this matrix material. Those components of the antigenic material to which the immobilized polyclonal antibodies are cross-reactive will be bound and will be immobilized by the matrix material. Those components of the antigenic material from the target microorganism which are immunologically distinguishable from antigenic material from the nontarget microorganism pass unbound over the matrix material. These unbound components are collected and may serve as the immunologically purified fraction of the antigenic material for use in the serum antibody assay of this invention.

The prior art taught only physical methods for purifying quantitative amounts of antigenic material for use in a serum antibody assay. The physical methods included various forms of fractionation. The elimination or concentration of any given antigenic component by these physical methods is fortuitous, unpredictable, and uncorrelated with the immunological properties of that antigenic component. Devising a process, a priori, using only physical methods for successfully separating an immunologically distinguishable antigenic component from crude antigen would be impractical. The immunological methods of this invention for purifying immunologically distinguishable antigenic material are novel. The use of this immunologically distinguishable antigenic material enables the novel serum antibody assay of this invention.

The serum antibody assay for detecting serum antibody directed against a target microorganism is novel because it uses components of antigenic material derived from the target microorganism which are immunologically purified and immunologically distinguishable from antigenic material dervied from a nontarget microorganism, by which use cross-reactive binding and false positives caused by antibody directed against a nontarget microorganism is essentially eliminated.

The serum antibody assay for detecting serum antibody directed against a target microorganism is novel because it uses immunologically distinguishable antigenic components obtained by a monoclonal method of immunological purification.

The serum antibody assay for detecting antibody to a target microorganism is novel because it uses immunologically distinguishable antigenic components obtained by a polyclonal method of immunological purification.

The antigenic reagents which include immunologically purified antigenic components attached to solid matrix materials are novel.

The immunological methods of this invention for obtaining immunologically distinguishable antigenic material are novel. Both the monoclonal method and the polyclonal method of immunological purification of antigen are novel.

The double screening method for selecting a hybridoma is novel because it selects monoclonal antibody having a binding specificity for a soluble fraction of antigenic material derived from a target microorganism and lacking a binding specificity for a soluble fraction of antigenic material derived from a nontarget microorganism.

DETAILED DESCRIPTION OF THE INVENTION

Before the invention can be practiced, a first preliminary step requires that the microorganism to which the antibody assay is to be targeted be specified. The antibody assay will usually test for the presence of only one microorganism and obviously the identity of that microorganism must be known before the antibody assay can be constructed. For purposes of illustration of this invention, the target microorganism has been chosen to be Dirofilaria immitis.

A second preliminary step to the practice of the invention is the identification of nontarget microorganisms which occur with a clinically significant frequency in the population to be tested by this antibody assay and to which antibodies arise which cross-react with the target microorganism or antigenic material derived from the target microorganism. Cross-reactive antibodies to such nontarget microorganisms can interfere with antibody assays of the prior art unless the serum sample from the test subject is pretreated, discussion supra. For purposes of illustration of this invention, the nontarget microorganism has been chosen to be Toxocara canis and the test population to be a species of the canis genus.

After the target microorganism, the nontarget microorganisms, and the test population are determined, the first task to the actual practice of this invention is the isolation of workable samples of antigenic materials derived from the target and nontarget microorganisms. It is easiest to work with a soluble fraction of the antigenic material.

I. Production of Soluble Fraction of Antigenic Materials:

One method for preparing D. immitis antigen extract is given as follows: Dirofilaria immitis (0.42 g), mixed males and females, are homogenized in 25 ml PBS for 2 minutes at 15 degrees Centigrade, and stored overnight at 4 degrees Centigrade. After centrifugation, the supernatant is acidified by addition of 10% trichloroacetic acid (TCA) to a pH of 3.5 at 15 degrees Centigrade. In some instances, it may be necessary to correct for excessive additions of TCA by addition of 1N sodium hydroxide to bring the pH back to 3.5. The fractionated antigen is then separated by centrifugation. The soluble protein in the supernatant is collected and dialyzed exhaustively against phosphate buffered saline buffer (PBS) at 4 degrees Centigrade.

T. canis antigen extract can be prepared by a method very similar to the method described above for preparing D. immitis antigen extract with only two modifications:

a. T. canis is substituted for D. immitis, and
b. The TCA fractionation step may be eliminated.

II. Production of Immunologically Purified Fraction of Antigenic Material:

The next step in the practice of the invention is the production of an immunologically purified fraction of the above antigenic material derived from the target microorganism so as to make the antigenic reagent for use in the antibody assay. The immunologically purified fraction of target antigenic material becomes nonreactive to antibody directed against the nontarget microorganism, even though such antibody is usually cross-reactive with nonimmunologically purified antigen extract of the target microorganism.

The invention teaches two methods for making an immunologically purified fraction of target antigenic material:

a. The monoclonal antibody method, and
b. The polyclonal antibody method.

Examples of each method of immunological purification are given below for the target microorganism D. immitis and the nontarget microorganism T. canis.

A. Monoclonal Antibody Method of Immunological Purification of D. immitis Antigen Extract:

Murine monoclonal antibodies which recognize the D. immitis antigen can be prepared as follows: The antigen is emulsified with complete Freunds adjuvant and 50 micrograms of antigen in 200 microliters of emulsion is injected into mice. After booster injections of similar composition at 1 week and 3 weeks, the mice are sacrificed. Their spleens are removed and placed in a 60 millimeter petri dish containing 4 milliliters of serum-free medium. A single suspension of splenocytes can be generated by teasing the spleen with forceps. The suspended splenocytes are then transferred to a 50 milliliter centrifuge tube and enough medium is added to yield a total volume of 40-45 milliliters. The splenocytes are then centrifuged for 10 to 15 minutes at 800 xg. After centrifugation, the pelleted splenocytes are washed by resuspension and a second centrifugation. The washed splenocytes are then brought up and resuspensed in 10 milliliters of media. Murine myeloma cells (cell line P3X63.Ag8.653) are then added to the washed splenocytes at a ratio of 1:6 myeloma cells to splenocytes. Then 0.35 milliliters of polyethylene glycol (PEG), which was melted in a water bath at 56 degrees Centigrade, is added to 0.65 milliliters of media at 37 degrees Centigrade. The PEG solution is then mixed and added to the cell mixture in a dropwise fashion, resulting in a fusion of the cells to form hybridomas. The fusion process is stopped by adding 9 milliliters of DMEM with 10% FBS to the cell mixture and then washed by centrifugation. The washed cells are placed into 200 milliliters of HAT medium containing $2 \times 10(6)$ thymocytes/milliliter. This cell suspension is then dispensed into eight 96 well plates (25 milliliters/plate) and incubated. At days 10 and 18, the media from each of the 96 well plates is removed and replaced with fresh media. The removed supernatants are assayed for anti-D. immitis and anti-T. canis antibodies by an enzyme immunoassay as described below. Hybridoma cell lines which are found to secrete monoclonal anti-D. immitis antibody and which are also found to not secrete anti-T. canis antibody are considered useful. The useful hybridoma cell lines are expanded in tissue culture. Samples of the expanded hybridoma cell lines are frozen in liquid nitrogen and put into storage. Aliquots of the hybridoma cell line are injected interperitoneally into mice to produce ascitic fluid containing the monoclonal antibody. After the production of monoclonal antibody, the ascitic fluid is collected and the monoclonal antibodies are isolated by precipitation with 50% saturated ammonium sulfate. The precipitate is then exhaustively dialyzed against phosphate buffered saline (PBS).

The immunoassay for screening the hybridomas for the production of anti-D. immitis antibody or the nonproduction of anti-T. canis antibodies may be an enzyme immunoassay constructed as follows: 96 well microtiter plates (e.g. from "Dynatek") are coated with either the D. immitis antigen extract or the T. canis antigen extract described above. Antigen coating will occur if each well is loaded with 100 to 200 nanograms of antigen extract in 50 microliters of sodium borate buffer. The antigen and sodium borate buffer are allowed to incubate in each well for four hours at 37 degrees Centigrade, followed by approximately 14 hours at 4 degrees Centigrade. After the incubation, unattached antigen is removed with the sodium borate buffer by decanting the fluid from each well. The wells are then washed three times with phosphate buffered saline containing 0.025% Tween 20. The washed plates are allowed to dry, leaving a coat of dry antigen attached to the well. Supernatants from hybridomas suspected of producing anti-D. immitis monoclonal antibodies are tested by placing 50 microliter aliquots into the D. immitis antigen coated wells. Similarly, supernatants from the screened hybridomas can be further tested for the nonproduction of T. canis by placing 50 microliter aliquots into the T. canis antigen coated wells. After a 30 minute reaction time, the supernatants are removed and the wells are washed three times with PBS containing 0.025% Tween 20.

To each washed well is added 150 microliters of goat anti-mouse IgG-HRP (horseradish peroxidase) enzyme conjugate in PBS pH 7.4, according to the method of Nakane (Nakane, P., et al, Histochem. and Cytochem., vol. 22, page 1084, (1974)). The plates are incubated for 30 minutes and then washed with PBS three times by decanting. ABTS (2,2'-azino-di-(3-ethylbenzthiazoline) sulfonic acid) 2 grams/80 milliliters of water is prepared and stored at 4 degrees Centigrade. Hydrogen peroxide 0.01% is prepared by dilution of 30% peroxide into water. To initiate HRP measurement, 50 microliters of ABTS and hydrogen peroxide are added to the wells. Color development depends upon enzyme concentration but is typically observed over 5 to 30 minutes. The development of color indicates that there is antibody in the supernatant which binds to the coated well and that hybridoma being tested does indeed produce anti-D. immitis antibody or does indeed produce anti-T. canis antibody, as the case may be.

Hybridoma supernatants which test positive for anti-D. immitis antibody and negative for anti-T. canis antibody indicate useful hybridoma cell lines which produce monoclonal antibody to be used in the immunological purification method for purifying the target antigenic material, e.g., the D. immitis antigen extract. The useful monoclonal antibodies are purified from murine ascites by ammonium sulfate precipitation, as described above. The purified monoclonal antibodies are then coupled to a polysaccharide gel material, such as "CNBr Sepharose" (made by Pharmacia), by a method according to Axen (Axen, R., et at, Nature, vol. 24, pages 1302–1304 (1967)) or by the method suggested by the manufacturer. The coupled monoclonal antibodies and the gel form an immunoadsorbent which can be used to adsorb and immobilize reactive antigenic material to the gel material.

The above immunoadsorbent can then be used to obtain a purified fraction of D. immitis antigen which is nonreactive with anti-T. canis antibodies. If the immunoadsorbent is a Sepharose immunoadsorbent, then 0.5 milliliters of the Sepharose monoclonal immunoadsorbent is combined and allowed to react with 1.0 milliliter of the D. immitis antigen extract for a period of 1 hour at 4 degrees Centigrade. Only antigenic components which are immunologically distinguishable from the nontarget microorganism, i.e., which are reactive to the monoclonal antibody, will bind to the immunoadsorbent. Components of the antigen extract which do not bind to the immunoadsorbent include all components to which anti-T. canis antibody is cross-reactive. The unbound components are then rinsed from the immunoadsorbent or decanted and washed from the immunoadsorbent. The bound component is then released from the immunoadsorbent using a releasing agent, e.g., a 10% molar glycine buffer at a pH of 2.8. The released antigenic component is then eluted from the immunoadsorbent and collected. The releasing activity of the released agent carried with the eluted antigenic component is then neutralized. If the releasing agent is the above glycine buffer, then the releasing agent may be neutralized using an inorganic base. The collected antigenic component comprises an immunologically purified fraction of the antigenic material which is immunologically distinguishable from the nontarget antigenic material.

The immunologically purified fraction of antigenic material is then immobilized onto a solid phase carrier to produce the antigenic reagent for use in the antibody assay, discussed infra.

B. Polyclonal Antibody Method of Immunological Purification of D. immitis Antigen Extract:

T. canis antigen extract (0.5 milligrams in 1 milliliter PBS) is emulsified with 1 milliliter of complete Freunds adjuvant. An aliquot of the emulsion, containing 50 micrograms of the antigen extract, is injected into a goat. After a booster injection at two weeks, serum containing anti-T. canis antibodies is obtained from the goat. The IgG fraction of the goat serum is purified by ammonium sulfate precipitation followed by exhaustive dialysis against PBS. A polyclonal immunoadsorbent is made by coupling the purified IgG fraction, including the anti-T. canis activity, to a polysaccharide gel, e.g. "CNBr-Sepharose," by a method as described above for the monoclonal immunoadsorbent.

The polyclonal immunoadsorbent is then used to immunologically purify a sample of the D. immitis antigen extract. An excess of polyclonal immunoadsorbent is incubated and allowed to react with 5.0 ml of the D. immitis antigen extract for 1 hour at 4 degrees Centigrade in PBS. The supernatant of the incubation mixture is separated from the immunoadsorbent by centrifugation and collected by decanting. The collected supernatant contains an immunologically purified fraction of the D. immitis antigen extract. The immunologically purified fraction contains antigenic components which are both reactive with anti-D. immitis antibodies and nonreactive with anti-T. canis antibodies. Substantially all components which are reactive anti-T. canis antibodies remain bound to the polyclonal immunoadsorbent at the decanting step. Application of a releasing agent to the immunoadsorbent and following a washing step allows the immunoadsorbent to be recycled. The immunologically purified fraction of D. immitis antigen extract is then used to construct an antigenic reagent as described below.

III. Production of the Antigenic Reagent:

The immunologically purified fraction of antigen extract is coupled to solid phase carrier to form an antigenic reagent. The antigenic reagent is used in the serum antibody assay of this invention, described infra. The essential novel feature of both the antigenic reagent and the antibody assay is the use of the immunologically purified fraction of the antigen extract. Many of the solid state carriers used by the prior art may be used to form the antigenic reagent. Two examples of different solid state carriers are provided to illustrate the invention: A.) microtiter plates, and B.) polymeric latex.

A. Microtiter Plates:

The solid state carrier may include any microtiter plate having a composition which can bind the immunologically purified antigenic material. Examples of microtiter plate compositions which can bind the immunologically purified antigenic material include plastic compositions such as polystyrene, polycarbonate, and polymethylacrylate. The binding mechanism may include electrostatic forces, hydrophobic forces, covalent forces, and other forces. If the solid state carrier is a standard polystyrene 96 well microtiter plate, then each well is loaded with 100 to 200 nanograms of the immunologically purified fraction in 50 microliters of a sodium borate buffer and allowed to incubate, as described above in the immunoassay for screening the hybridomas. The immunologically purified fraction may include either the component obtained by the monoclonal immunoadsorption method or obtained by the polyclonal immunoadsorption method, described above. After the incubation, the wells are washed and allowed to dry, leaving a coat of the immunologically purified fraction. The coat of the microtiter plate includes the immunologically purified fraction of anti-D. immitis antibody which is immunologically distinguishable from T. canis antigen and which is nonreactive to anti-T. canis antibodies. The coated microtiter may then be used in the corresponding antibody assay described below. During the serum antibody assay described below, these microtiter plates will bind anti-D. immitis antibodies but will not bind anti-T. canis antibodies.

B. Polymeric Latex:

The solid state carrier may include a polymeric latex material. In this event, the antigenic reagent includes and becomes a latex agglutination reagent. The latex agglutination reagent may be prepared by coating polystryene latex according to the method of Singer (Singer, J. M., et al, American Journal of Medicine, vol. 21, pages 888-892, (1956)). Again, the immunologically purified fraction which coats the solid state carrier may include D. immitis antigen purified by either the monoclonal immunoadsorption method or the polyclonal immunoadsorption method described above. The specially coated latex agglutination reagent is then used in an antibody assay which includes an agglutination step as described in Singer.

IV. The Antibody Assay

Although all protocols for the various antibody assays of this invention require the use of an immunologically purified fraction of the target antigenic material which is immunologically distinguishable from nontarget antigen, the particular protocol for a given assay will depend upon the particular solid phase carrier used to construct the antigenic reagent. However, the distinguishing feature of the serum antibody assays of this invention is that these serum antibody assays eliminate the problem of cross-reactivity. Antibody assays are illustrated for the two examples given for the of antigenic reagent described above, viz. the microtiter plates and the agglutination reagent.

A. Antibody Assay using Microtiter Plates:

Canine serum is assayed for the presence of anti-D. immitis antibodies by placing 50 microliter aliquots into the immunologically purified D. immitis antigen coated wells of the microtiter plate type antigenic reagent. After a 30 minute reaction time, the canine serum is removed and the wells are washed three times with PBS containing 0.025% Tween 20.

To each washed well is added 150 microliters of goat anti-canine IgG-HRP (horseradish peroxidase) enzyme conjugate in PBS pH 7.4, according to the method of Nakane (supra). The plates are incubated for 30 minutes and then washed with PBS three times by decanting. ABTS (2,2'-azino-di-(3-ethylbenzthiazoline) sulfonic acid) 2 grams/80 milliliters of water is prepared and stored at 4 degrees Centigrade. Hydrogen peroxide 0.01% is prepared by dilution of 30% peroxide into water. To initiate HRP measurement, 50 microliters of ABTS and hydrogen peroxide are added to the wells. Color development depends upon enzyme concentration but is typically observed over 5 to 30 minutes. The development of color indicates that there is anti-D. immitis antibody in the canine serum being tested. The presence of anti-T. canis antibody in the canine serum sample will not cause color development in the microtiter well in normal operation.

Equivalent conjugates may also be employed. The goat anti-canine IgG may be replaced by anti-sera from other non-canine species. The conjugated HRP may be replaced by equivalent labels employed by other immunoassays of the prior art. Such labels include a variety of enzymes, fluorophors, radionuclides, chemiluminigenic compounds, enzyme cofactors, and enzyme inhibitors.

Comparative tests were made using microtiter plates coated with D. immitis antigen extract (not immunoadsorbed) and with immunologically purified antigen as required by the invention. The antibody assay described above was performed using these two types of microtiter plates on a panel of canine serum samples obtained from dogs known not to be infected by D. immitis, as determind upon autopsy or by the immunofluorescence assay (IFA) described by M. Wong (Wong, M., and Guest, M., Transactions of the Royal Society of Tropical Medicine and Hygiene, vol. 63, pages 796-800, (1969)). A significant portion (30%) showed a false positive result with the microtiter plates coated with non-immunoadsorbed D. immitis antigen extract. In contrast, about 95% of these false positives did not show a positive response using the immunologically purified antigenic reagent. Pretreatment of the false positives samples with 50 microliters of T. canis antigen extract, 0.5 milligrams of extract/ milliliter to 100 microliters/sample, as taught by Grieve, also resulted in a nearly complete diminution in false positive reactions, i.e., essentially the same result as obtained by the antibody assay of this invention.

Samples obtained from dogs known to be infected by adult D. immitis showed the expected positive response with either antigenic reagent.

B. Antibody Assay using an Agglutinizing Reagent:

Canine serum is assayed for the presence of anti-D. immitis antibodies using the agglutinizing reagent, i.e., the polystyrene latex coated with the immunologically purified D. immitis antigen as described above. The protocol for the agglutinizing antibody assay substantially follows Singer's "latex fixation test" (cited above), except that the present assay uses canine serum and polystyrene latex is coated with the immunologically purified D. immitis angtigen. An assay which results in agglutination indicates that there is anti-D. immitis antibody in the canine serum being tested. On the other hand, the presence of anti-T. canis antibody in the canine serum sample will not cause agglutionation in the present assay in normal operation.

Comparative tests were made using the agglutination reagent coated with D. immitis antigen extract (not immunoadsorbed) and with the immunologically purified antigen required by the invention. The agglutination antibody assay described by Singer was performed using these two types of agglutination reagents on a panel of canine serum samples obtained from dogs known not to be infected by D. immitis as determined upon autopsy, or by immunofluorescence assay (IFA) cited above (Wong), a significant portion (30%) showed a false positive agglutination with the non-immunoadsorbed D. immitis antigen latex reagent. In contrast, 95% of the false positives did not agglutinate the immunologically purified D. immitis antigen latex reagent. Pretreatment of the false positive samples with 50 microliters of T. canis antigen extract, 0.5 milligrams of extract/milliliter to 100 microliters/sample also resulted in a nearly complete diminution in false positive reactions, as taught by Grieve.

Samples obtained from dogs known to be infected by adult D. immitis showed the expected positive agglutination for either the non-immunoadsorbed antigen latex or the immunologically purified antigen latex.

These comparative tests demonstrate that the present invention teaches a method for determining the presence of anti-D. immitis antibodies in serum containing T. canis antibodies without interference by cross-reactive anti-T. canis antibodies and without the need for a pretreatment of the test serum.

What is claimed is:

1. In an assay for detecting anti-Dirofilaria immitis antibody in a serum sample, the assay including the following steps:
    step (a): contacting the serum sample with an immunoassay reagent having soluble antigenic components of Dirofilaria immitis attached thereto for binding the anti-Dirofilaria immitis antibody, and then
    step (b): detecting the anti-Dirofilaria immitis antibody bound to the immunoassay reagent,
wherein an improvement enables the antibody assay to discriminate between the detection of anti-Dirofilaria immitis antibody and the detection of anti-Toxocara canis antibody, the improvement comprising:
    in said contact step (a) and said detection step (b), the soluble antigenic components of Dirofilaria immitis which are attached to the immunoassay reagent consist essentially of non-cross-reactive antigenic subcomponents which are reactive with anti-Dirofilaria immitis antibody and are non-cross-reactive with anti-Toxocara canis antibody, and
    said detection step (b) being insensitive to the presence or absence of anti-Toxocara canis antibody.

2. The assay as described in claim 1, wherein:
    the immunoassay reagent including an agglutinizing reagent which undergoes an agglutination reaction upon contact with anti-Dirofilaria immitis antibody both in the presence and absence of anti-Toxocara canis antibody,
    said detection step (b) being dependent upon the agglutination reaction.

3. The assay as described in claim 1, wherein:
    the immunoassay reagent including a solid phase carrier for the attachment of the non-cross-reactive antigenic subcomponents of Dirofilaria immitis, and
    the antibody assay further comprising the following additional step between step (a) and step (b):
    step (c): washing the solid phase carrier of the immunoassay reagent to remove unbound components of the serum sample, and wherein
    said detection step (b) employing a labelled conjugate of anti-IgG for detecting the presence of bound anti-Dirofilaria immitis, the labelled conjugate including a label selected from the group consisting of enzymes, fluorophors, radionuclides, chemiluminigenic compounds, enzyme cofactors, and enzyme inhibitors.

4. A method for purifying soluble non-cross-reactive antigenic components of Dirofilaria immitis from a crude extract of Dirofilaria immitis, the soluble non-cross-reactive antigenic components being non-cross-reactive with anti-Toxocara canis antibody, the crude extract including cross-reactive subcomponents which are cross-reactive with both anti-Dirofilaria immitis antibody and anti-Toxocara canis antibody, the method comprising the following steps:
    step (a): incubating the crude extract of Dirofilaria immitis with a solid phase immunoadsorbent having anti-Toxocara canis antibody attached thereto for binding the cross-reactive subcomponents, and then
    step (b): eluting and collecting the unbound soluble non-cross-reactive antigenic components of the crude extract from the solid phase immunoadsorbant without eluting the bound cross-reactive subcomponents,
    whereby the collected soluble non-cross-reactive antigenic component is substantially free of the cross-reactive antigenic subcomponent.

5. A monoclonal antibody reactive with an antigenic extract of Dirofilaria immitis and non-cross-reactive with an antigenic extract of Toxocara canis.

6. In an immunoassay reagent for use in an antibody assay for detecting anti-Dirofilaria immitis antibody in a serum sample, the immunoassay reagent including:
    a solid phase carrier and
    soluble antigenic components of anti-Dirofilaria immitis,
    said antigenic components being attached to said solid phase carrier for binding and immobilizing anti-Dirofilaria immitis antibody,
    wherein an improvement enables the antibody assay to discriminate between the detection of anti-Dirofilaria immitis antibody and the detection of anti-Toxocara canis antibody, the improvement comprising:
    said soluble antigenic components consisting essentially of non-cross-reactive antigenic subcomponents which are reactive with anti-Dirofilaria immitis antibody and non-cross-reactive with anti-Toxocara canis antibody.

7. In an immunoassay reagent for use in an antibody assay for detecting anti-Dirofilaria immitis antibody in a serum sample, the immunoassay reagent including:
    an agglutinizing reagent and
    soluble antigenic components of anti-Dirofilaria immitis,
    said antigenic components being attached to said agglutinizing reagent for binding and agglutinating anti- Dirofilaria immitis antibody,
    wherein an improvement enables the antibody assay to discriminate between the detection of anti-Dirofilaria immitis antibody and the detection of anti-Toxocara canis antibody, the improvement comprising:

said soluble antigenic components consisting essentially of non-cross-reactive antigenic subcomponents which are reactive with anti-Dirofilaria immitis antibody and non-cross-reactive with anti-Toxocara canis antibody.

8. A method for purifying a crude extract of Dirofilaria immitis to obtain soluble antigenic components which are reactive with anti-Dirofilaria immitis antibody and which are non-cross-reactive with anti-Toxocara canis antibody, the method comprising the following steps:

step (a): combining and incubating the crude extract of Dirofilaria immitis with a solid phase immunoadsorbent including an anti-Dirofilaria immitis monoclonal antibody attached thereto, the anti-Dirofilaria immitis monoclonal antibody having a binding specificity for soluble antigenic components which are non-cross-reactive with anti-Toxocara canis antibody, then step (b): washing the immunoadsorbent to remove unbound components of the crude extract, then step (c): eluting the bound soluble antigenic components from the immunoadsorbent by rinsing with a releasing agent, and then step (d): collecting the eluted soluble antigenic components and neutralizing the collected releasing agent, the eluted soluble antigenic components being reactive with anti-Dirofilaria immitis antibody and non-cross-reactive with anti-Toxocara canis antibody

* * * * *